US006741730B2

(12) United States Patent
Rahn et al.

(10) Patent No.: US 6,741,730 B2
(45) Date of Patent: May 25, 2004

(54) METHOD AND APPARATUS FOR THREE-DIMENSIONAL IMAGING IN THE FOURIER DOMAIN

(75) Inventors: J. Richard Rahn, Sammamish, WA (US); Alan C. Nelson, Gig Harbor, WA (US)

(73) Assignee: Visiongate, Inc., Gig Harbor, WA (US)

(*) Notice: Subject to any disclaimer, the term of this patent is extended or adjusted under 35 U.S.C. 154(b) by 9 days.

(21) Appl. No.: 10/307,712

(22) Filed: Dec. 2, 2002

(65) Prior Publication Data

US 2003/0118223 A1 Jun. 26, 2003

Related U.S. Application Data

(63) Continuation-in-part of application No. 09/927,151, filed on Aug. 10, 2001, now Pat. No. 6,522,775.

(51) Int. Cl.$^7$ ................................................. G06K 9/00
(52) U.S. Cl. ................................................. 382/131
(58) Field of Search ................................ 382/131, 333, 382/280; 250/455.11, 461.2, 339.08; 353/28; 378/8, 11, 23; 377/10; 359/559, 564

(56) References Cited

U.S. PATENT DOCUMENTS

| | | | |
|---|---|---|---|
| 3,470,373 A | 9/1969 | Brewer ..................... 250/461.2 |
| 3,497,690 A | 2/1970 | Wheeless, Jr. ............. 250/461.2 |
| 3,598,471 A | * 8/1971 | William et al. ............. 359/562 |
| 3,657,537 A | 4/1972 | Wheeless, Jr. ............. 250/461.2 |
| 3,748,468 A | * 7/1973 | Hartman ..................... 250/311 |
| 3,833,762 A | 9/1974 | Gudmundsen ......... 348/208.99 |
| 3,960,449 A | 6/1976 | Carlton et al. ............. 356/340 |
| 3,999,047 A | 12/1976 | Green ......................... 382/134 |
| 4,175,860 A | 11/1979 | Bacus ......................... 356/39 |
| 4,200,353 A | * 4/1980 | Hoffman ..................... 359/370 |
| 4,293,221 A | 10/1981 | Kay ........................... 356/318 |
| 4,360,885 A | 11/1982 | Edgar ......................... 382/131 |
| 4,387,989 A | * 6/1983 | Pirich ......................... 356/71 |
| 4,873,653 A | 10/1989 | Grosskopf ................... 359/371 |
| 5,141,609 A | 8/1992 | Sweedler et al. ............ 204/452 |
| 5,148,502 A | 9/1992 | Tsujiuchi et al. ............ 384/255 |
| 5,281,517 A | 1/1994 | Bacus et al. .................. 439/6 |
| 5,308,990 A | 5/1994 | Takahashi et al. ........ 250/459.1 |
| 5,312,535 A | 5/1994 | Waska et al. ................ 204/603 |
| 5,402,460 A | 3/1995 | Johnson ....................... 378/10 |
| 5,668,887 A | 9/1997 | Parker et al. ................ 384/108 |
| 5,680,484 A | 10/1997 | Ohyama et al. ............. 382/255 |
| 5,710,429 A | * 1/1998 | Alfano et al. ............. 250/358.1 |
| 5,741,411 A | 4/1998 | Yeung et al. ................ 204/452 |

(List continued on next page.)

FOREIGN PATENT DOCUMENTS

SU 1183934 A 10/1985 ........... G02B/21/00

OTHER PUBLICATIONS

Kikuchi, S. et al., "Three–dimensional computed tomography for optical microscopes," Optics Communications 107 (1994) 432–444.

Kikuchi, S. et al., "Three–dimensional microscopic computed tomography based on general Radon transform for optical imaging systems," Optics Communication 123 (1996).

Matula, P. et al. "Precise 3D image alignment in micro–axial tomography," Journal of Microscopy, vol. 209, Pt. 2 (Feb. 2003) pp. 126–142.

(List continued on next page.)

Primary Examiner—Andrew W. Johns
Assistant Examiner—Shervin Nakhjavan
(74) Attorney, Agent, or Firm—George A. Leone

(57) ABSTRACT

Two or more two-dimensional Fourier transforms are acquired from different perspectives of a three-dimensional object region. A three-dimensional Fourier transform is then constructed using tomographic methods, permitting the application of image analysis algorithms analogous to those used for two-dimensional images.

23 Claims, 4 Drawing Sheets

U.S. PATENT DOCUMENTS

| | | | | |
|---|---|---|---|---|
| 5,828,408 | A | | 10/1998 | Mottin et al. ............... 348/295 |
| 5,848,123 | A | | 12/1998 | Strommer .................. 378/98.8 |
| 5,878,103 | A | | 3/1999 | Sauer et al. ................ 378/115 |
| 5,880,838 | A | * | 3/1999 | Marx et al. ................. 356/498 |
| 5,909,476 | A | | 6/1999 | Cheng et al. .................. 378/4 |
| 5,987,158 | A | | 11/1999 | Meyer ........................ 382/135 |
| 6,005,617 | A | | 12/1999 | Shimamoto et al. ........ 348/295 |
| 6,026,174 | A | | 2/2000 | Palcic ......................... 382/133 |
| 6,047,080 | A | | 4/2000 | Chen et al. ................ 382/128 |
| 6,091,983 | A | * | 7/2000 | Alfano et al. .............. 600/431 |
| 6,130,958 | A | | 10/2000 | Rohler et al. .............. 382/131 |
| 6,165,734 | A | | 12/2000 | Garini ....................... 435/7.21 |
| 6,201,628 | B1 | | 3/2001 | Basiji ......................... 359/212 |
| 6,211,955 | B1 | | 4/2001 | Basiji ......................... 356/326 |
| 6,215,587 | B1 | * | 4/2001 | Alfano et al. .............. 359/368 |
| 6,248,988 | B1 | | 6/2001 | Krantz .................... 250/201.3 |
| 6,249,341 | B1 | | 6/2001 | Basiji ......................... 356/173 |
| 6,251,586 | B1 | | 6/2001 | Mulshine ...................... 435/6 |
| 6,251,615 | B1 | | 6/2001 | Oberhardt .................. 435/2.21 |
| 6,252,979 | B1 | | 6/2001 | Lee ............................ 382/133 |
| 6,452,179 | B1 | * | 9/2002 | Coates et al. .......... 250/339.09 |
| 6,529,614 | B1 | * | 3/2003 | Chao et al. ................. 382/103 |
| 2001/0012069 | A1 | | 8/2001 | Derndinger et al. ........ 348/295 |
| 2002/0161534 | A1 | | 10/2002 | Adler et al. .................. 702/35 |

OTHER PUBLICATIONS

Ong, SH, Development of an imaging flow cytometer. Anal Quant Cytol Histol 9(5)pp. 375–382, 1987.

Gilbert, P, "Iterative Methods for the Three dimensional Reconstruction of an Object from Projections," Journal of Theoretical Biology 36pp. 105–117, 1972.

Oppenheim, BE, More Accurate Algorithms for Iterative 3 dimensional Reconstruction, IEEE Transactions on Nuclear Science NS–21pp. 72–77, 1974.

Singer, JR, Grunbaum, FA, Kohn, P, and Zubelli, JP, "Image Reconstruction of the Interior of Bodies that Diffuse Radiation," Science 248 (4958)pp. 990–993, 1990.

Mueller, K and Yage, R, "Rapid 3–D Cone–beam Reconstruction with the Simultaneous Algebraic Reconstruction Technique (SART) Using 2–D Texture Mapping Hardware", IEEE Transactions on Medical imaging 19(12)pp. 1227–1237, 2001.

Bellman, SH, Bender, R, Gordon, R, and Rowe, JE, "Art is Science being A Defense of Algebraic Reconstruction Techniques for Three dimensional Electron Microscopy," Journal of Theoretical Biology 32pp. 205–216, 1971.

Manglos, SH, Jaszcak, RJ, and Floyd, CE, "Maximum Likelihood Reconstruction for Cone Beam SPECT: Development and Initial Tests," Physics in Medicine and Biology 34(120)pp.1947–1957, 1989, #1382.

Manglos, SH, Gagne, GM, Krol A, Thomas FD, and Narayanaswamy, R, "Transmission Maximum–likelihood Reconstruction with Ordered Subsets for Cone Beam CT", Physics in Medicine and Biology 40(7)pp. 1225–1241, 1995 #4389.

Hampel, U and Freyer, R, "Fast Image Reconstruction for Optical Absorption Tomography in Media with Radially Symmetric Boundaries", Medical Physics 25 (1)pp. 92–101, 1998.

Jiang, H, Paulsen, KD, and Osterberg, UL, "Frequency–domain Near–infared Photo Diffusion Imaging: Initial Evaluation in Multitarget Tissuelike Phantoms", Medical Physics 25(2)pp. 183–193, 1998.

Herman, G, *Image Reconstruction from Projections: The Fundamentals of Computerized Tomography*, Academic Press, New York, 1980.

Paulsen, KD and Jiang, H, "Spatially Varying Optical Property Reconstruction Using a Finite Element Diffusion Equation Approximation", Medical Physics 22(691–701) 1995.

Farichild Imaging, Preliminary Data Sheet CCD525, TDI, Time Delay and Integration Sensor, Jan. 12, 2001.

Farichild Imaging, Preliminary Data Sheet CCD582, TDI, Time Delay and Integration Sensor, Jan. 18, 2000.

Shapiro, HM, *Practical Flow Cytometry*, $3^{rd}$ ed., Wiley-Liss, 1995.

Bayat, S, Le Duc, G, Porra, L, Berruyer, G, Nemoz, C, Monfraix, S, Fiedler, S, Thomlinson, W, Suortti, P, Standertskjold–Nordenstam, CG, and Sovijarvi, ARA, "Quantitative Functional Lung Imaging with Synchrotron Radiation Using Inhaled Xenon as Contrast Agent", Physics in Medicine and Biology 46(3286–99) 2001.

Bently, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282(R1267–R1279) 2002.

Cheng, PC, Lin, TH, Wang, G, Shinozaki, DM, Kim, HG, and Newberry, SP, "Review on the Devleopment of Cone–beam X–ray Microtomography", Proceedings of the X–ray Optics and Microanalysis 1992, Institute of Physics Ser. No. 130, Kenway, PB, et al. (eds.), Manchester, UK, Aug. 31–Sep. 4, 1992, pp. 559–566.

Defrise, M, Clack, R, and Townsend, DW, "Image Reconstruction from Truncated, Two–dimensional, Parallel Projections", Inverse Problems 11(287–313) (1995).

Defrise, M, Noo, F, and Kudo, H, "A Solution to the Long–object Problem in Helical Cone–beam Tomography", Physics in Medicine and Biology 45(623–43) 2000.

Endo, M, Tsunoo, T, Nakamori, N, and Yoshida, K, "Effect of Scattered Radiation on Image Noise in Cone Beam CT", Medical Physics 28(4) (469–74) 2001.

Jorgensen, SM, Demirkaya, O, and Ritman, EL, "Three Dimensional Imaging of Vasculature and Parenchyma in Intact Rodent Organs with X–ray Micro–CT", Am. J. Physiology 275(Heart Circ. Physiol. 44) pp. H1103–H1114, 1998.

Kinney, JH, Johnson, QC, Saroyan, RA, Nichols, MC, Bonse, U, Nusshardt, R, and Pahl, R, "Energy–modulated X–ray Microtomography", Rev. Sci. Instrum. 59(1)pp.196–197, 1988.

Kinney, JH and Nichols, MC, "X–ray Tomographic Microscopy (XTM) Using Synchrotron Ratiation", Annu. Rev. Mater. Sci. 22pp. 121–152, 1992.

Taguchi, K and Aradate, H, "Algorithm for Image Reconstruction in Multi–slice Helical CT", Medical Physics 25(4) pp. 550–561, 1998.

Yu, DF, Fessler, JA, and Ficaro, EP, "Maximum–Likelihood Transmission Image Reconstruction for Overlapping Transmission Beams", IEEE Transactions on Medical Imaging 19(11)pp. 1094–1105, 2000.

E.G. Steward, *Fourier Optics: An Introduction*, 2nd ed. (Halsted Press, New York, 1987).

A. Klug and J.L. Finch, "Structure of viruses of the papilloma–polyoma type," J. Mol. Biol., vol. 37, p. 1 (1968).

A. Klug, "Image analysis and reconstruction in the electron microscopy of biological macromolecules," Chem. Scripta, vol. 14, p. 245 (1978).

T.C. Wedberg and J.J. Stamnes, "Recent results in optical diffraction microtomography," Meas. Sci. Technol., vol. 7, p. 414 (1996).

Y. Li, et al., "Comparison of analog and digital Fourier transforms in medical image analysis," J. Biomed. Optics, vol. 7, p. 255 (2002).

Y. Xu et al., "Three-dimensional diffuse optical tomography of bones and joints," J. Biomed. Optics, vol. 7, p. 88 (2002).

H. Bandagamboa et al., "Spectral-Analysis of Cervical Cells Using the Discrete Fourier-Tranform" Anal. Cell. Path., vol. 5(2), pp. 85–102 (1993).

D.E. Burger, et al., "Extraction of Morphilogical Features from Biological Models and Cells by Fourier Analysis of Static Light Scatter Measurements," Cytometry, vol. 2, No. 5, pp. 327–336 (1982).

M. Rozycka, et al., "Optical Diffraction as a Tool for Semiautomatic, Quantitative Analysis of Tissue Specimens," Cytometry, vol. 2, No. 4, pp. 244–248 (1982).

Almeida and Fuji, Fourier transform differences and averaged simularities in diatoms, Applied Optics, vol. 18, No. 10, pp. 1663–1667, (1979).

Smolinska and Dawidowicz, "Extraction of common or different part from optical images," Institute of Physics, Warsaw Technical University, 222–223.

Miles, CP, Jaggard, DL, "The Use of Optical Fourier Transforms to Diagnose Pleomorphism, Size and Chromatin Clumping in Nuclear Models," Anal Quant Cytol Histol vol. 3, No. 2, pp. 149–156, 1981.

Dziedzic–Goclawsak, et al., "Application of the Optical Fourier Transform for Analysis of the Spatial Distribution of Collagen Fibers in Normal and Osteopetrotic Bone Tissue," Histochemistry (1982) 74:123–137.

Ostrowski, et al., "Application of Optical Diffractometry in Studies of Cell Fine Structure," Histochemistry (1983) 78:435–449.

Mareel, MM, et al., "Numerical Evaluation of Changes in the Cytoplasmic Microtubule Complex of C3H Mouse Cells by Optical Diffractometry and of Changesin Cell Shape by Fourier Analysis," Cytometry 7:18–24 (1986).

Bem, W, et al., "Modification of Chromatin Pattern in the course of Terminal Differentiation During Human Granulocytopiesis: Optical Diffractometry Study," Cellular and Molecular Biology 33(5), 563–571 (1987).

Rozycka, M, et al., "Analysis of Chromatin Pattern in blood lymphocytes of healthy donors and in lymphoid cells of patients with chronic lymphocytic leukaemia," J. Clin. Pathol. 1988:41:540–509.

* cited by examiner

METHOD AND APPARATUS FOR THREE-DIMENSIONAL IMAGING IN THE FOURIER DOMAIN

This is a continuation in part (CIP) of U.S. patent application Ser. No. 09/927,151, filed Aug. 10, 2001, entitled "Apparatus and Method for Imaging Small Objects in a Flow Stream Using Optical Tomography," issued on Feb. 18, 2003 as U.S. Pat. No. 6,522,775 to Nelson which is incorporated herein by this reference.

FIELD OF THE INVENTION

The present invention relates to a three-dimensional imaging system in general, and, more particularly, to high-resolution optical tomography where the features of interest are of a size comparable to the wavelength of the light used to illuminate the objects of interest.

BACKGROUND OF THE INVENTION

A tomography device is intended to produce three-dimensional reconstructions of objects by providing a measure of light or x-ray attenuation along a set of ray paths through the object. Thus the existence of a focal plane within the object region is forbidden, i.e., the depth of field is infinite, and all the photons reaching an individual detector pixel element have, ideally, traveled along the same geometric path. For x-ray tomography, scattering from inhomogeneities within the object region is not an issue, because the size of such features is typically much larger than the wavelength of the incident radiation. In optical tomography, however, the wavelengths are much longer than they are in the case of x-ray tomography. Therefore, scattering from features within the object region can introduce noise into the system by causing several light rays to reach the same individual detector element after traveling along several different paths between the source and that detector element. The present invention exploits such scattering effects to acquire information about a three-dimensional object region, and re-arranges that information by mapping the spatial-frequency domain (k-space) into real space.

A. C. Kak and M. Slaney, in their book entitled *Principles of Computerized Tomographic Imaging* (IEEE Press, 1988), describe the use of the Fourier Slice Theorem to map transmitted or reflected light from the spatial domain into the frequency domain, as depicted in FIG. 1. By obtaining projection images from multiple viewpoints and applying a two-dimensional Fourier transform to each one, a set of planar surfaces through the frequency domain (k-space) can be generated. The sum of these planar surfaces can then be operated upon by a three-dimensional inverse Fourier transform to yield a three-dimensional reconstruction of the object region. In the presence of weak scattering within the object region, the planar surfaces become spherical surfaces, and the Fourier Diffraction Theorem should be substituted for the Fourier Slice Theorem. However, both of these approaches break down when strong scattering is present. The Fourier transform of a single projection maps a set of spherical surfaces through k-space, resulting in ambiguous values when the surfaces from different viewpoints are summed.

Work by Pernick, et al. (1978), Wohlers, et al. (1978), and Backman, et al. (2001) has demonstrated the usefulness of examining biological material in the two-dimensional Fourier domain. (See, for example, B. Pernick et al., "Screening of cervical cytological samples using coherent optical processing. Part 1," *Appl. Optics* 17, 21 (1978), R. Wohlers et al., "Screening of cervical cytological samples using coherent optical processing. Part 2," *Appl. Optics* 17, 35 (1978), B. Pernick et al., "Screening of cervical cytological samples using coherent optical processing. Part 3," *Appl. Optics* 17, 43 (1978), B. J. Pernick et al., Paraxial analysis of light scattering by biological cells in a flow system," *Appl. Optics* 17, 3205 (1978), V. Backman et al., "Measuring Cellular Structure at Submicrometer Scale with Light Scattering Spectroscopy," *IEEE J. Selected Topics Quantum Electron.* 7, 887 (2001)).

Techniques for using light diffraction to examine small features in an object have been described by Kopp, et al. in U.S. Pat. No. 4,150,360, issued Apr. 17, 1979, entitled "Method and Apparatus for Classifying Biological Cells," and U.S. Pat. No. 4,213,036 issued Jul. 15, 1980 entitled "Method for Classifying Biological Cells." Kopp, et al. used Fourier optics to acquire a single two-dimensional Fourier transform of a biological cell. However, three-dimensional object regions were not considered by Kopp, et al. In contrast, the method and apparatus of the present invention acquires multiple two-dimensional Fourier transforms from several different viewpoints. Using the different viewpoints, a three-dimensional Fourier transform is computed using conventional image reconstruction techniques that may be modified according to the specific geometric configuration.

In contrast to known methods, the present invention provides a method that allows real-time, in-situ processing of the light passing through the entire volume of the specimen region. The method of the present invention uses Fourier optics to map the angular distribution of light exiting the object region into real space at the back focal plane of a lens or mirror system. As a result, the three-dimensionality of the object region ceases to pose a problem, since in optical tomography the light rays need not originate within a single plane.

SUMMARY OF THE INVENTION

The present invention provides a method and apparatus for multi-dimensional imaging of an object region. The method includes the step of passing collimated light through an object region to produce transmitted light rays. In another step, the transmitted light rays are captured by at least one optical element, each of said at least one optical element having a back focal plane. At least one detector is used to capture a power distribution of a two-dimensional Fourier transform, where the at least one detector is located in a back focal plane of the least one optical element. For two or more viewpoints, the steps of the method are repeated about an arc at least partially encircling the object region to obtain multiple two-dimensional Fourier transforms.

BRIEF DESCRIPTION OF THE DRAWINGS

FIG. 2A schematically shows a more detailed view of the object region of FIG. 2 as contemplated by an embodiment of the present invention.

DETAILED DESCRIPTION OF THE PREFERRED EMBODIMENTS

Figure 1:
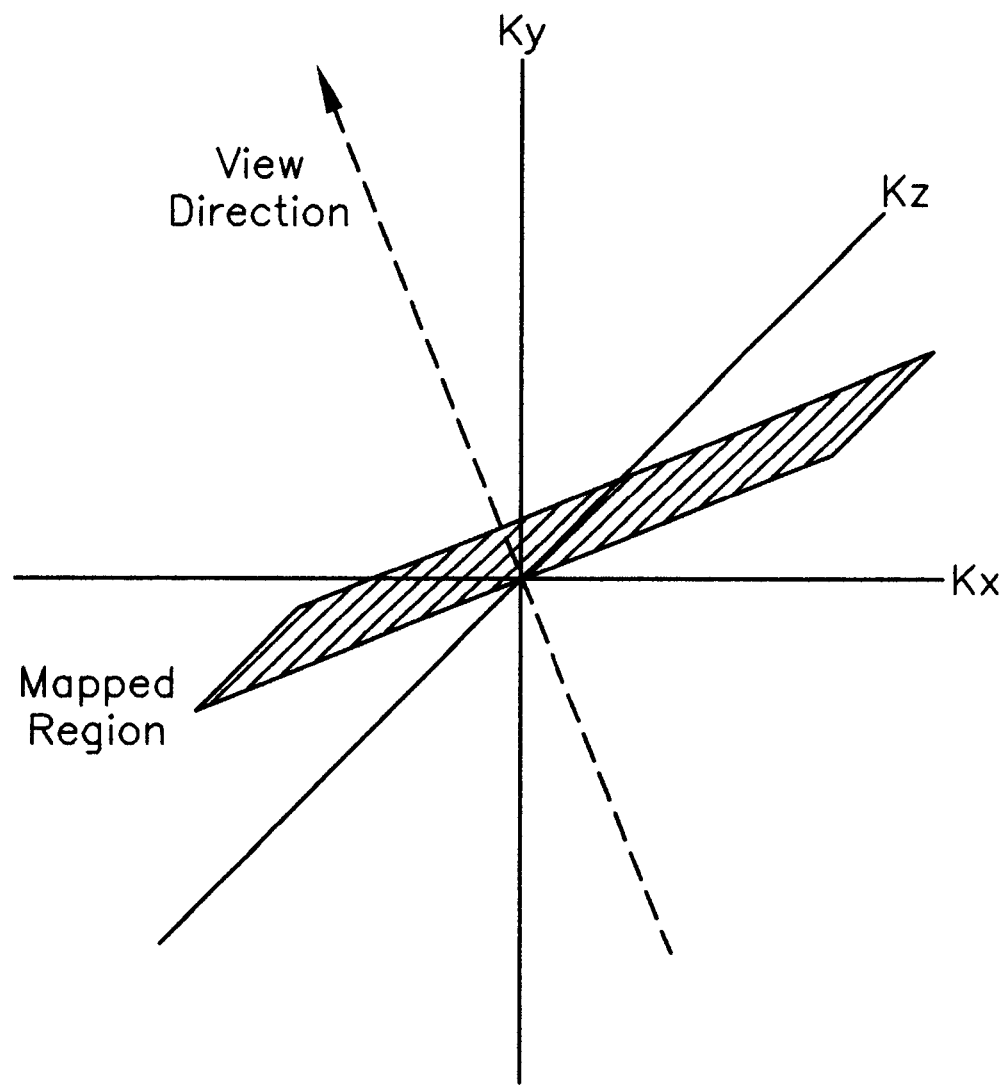
FIG. 1 illustrates the Fourier Slice Theorem.

The method and apparatus of the present invention do not require any assumptions about the strength of light scattering. Instead, the present invention takes advantage of the fact that a measurement of the intensity pattern in the back focal plane of a lens yields the magnitude of a Fourier transform of the light rays reaching the lens. A measured intensity pattern from an x-ray projection, on the other hand, can be transformed using Fourier transformation relationships to yield both real and imaginary components of a plane in k-space. In the present invention, the results of the Wiener-Khintchine Theorem can be applied. The Wiener-Khintchine Theorem states that the autocorrelation function, $C_{gg}$, of an object, $g(x,y)$, is equal to the inverse Fourier transform of the squared magnitude of the Fourier transform of the object:

$$c_{gg} = F^{-1}[|F(g)|^2]$$

where F and $F^{-1}$ represent the Fourier transform and the inverse Fourier transform operators, respectively. In a manner similar to the application of the Fourier Slice Theorem in non-diffracting systems, the intensity in the back focal plane of the lens from each of multiple viewpoints can be measured to find $|F(g)|^2$ for each plane in k-space. An inverse three-dimensional Fourier transform, $F^{-1}$, can then be applied to the sum to yield the three-dimensional autocorrelation function.

The Wiener-Khintchine Theorem is a special case of Parseval's Theorem, which states that the cross-correlation function, $c_{gh}$, of two objects $g(x,y)$ and $h(x,y)$, is equal to the inverse Fourier transform of their Fourier transforms:

$$c_{gh} = F^{-1}[F(g)F^*(h)]$$

where F* indicates the complex conjugate of the Fourier transform F.

In addition to using the present invention to generate auto-correlation and cross-correlation information, the measured values can be used directly, enabling image analysis methods to look for specific features in diffraction patterns.

The method and apparatus of the invention uses Fourier optics in an optical tomography device to pass substantially all the light exiting the object region, as limited by the aperture of a lens system. In accordance with one embodiment of the invention, the two-dimensional Fourier transform is mapped at the back focal plane of the lens system. Multiple views provide the ability to construct a three-dimensional Fourier transform and to use the information contained in this Fourier transform to extract information about the object region.

The method and apparatus of the present invention is based, in part, on the following principles. Fine features, such as a small object or a closely spaced grating, are said to have a high spatial frequency. Due to their high spatial frequency, fine features produce large deflections of the light rays that meet them. Conversely, coarse features are said to have a low spatial frequency, and deflect light rays only by a small amount. In conventional imaging, elimination of the high spatial frequencies will cause a loss of resolution in the image due to smoothing out of edges and small features, while eliminating the low spatial frequencies will produce an "outline" of the image, with sharp edges but without filled-in spaces.

Figure 2:
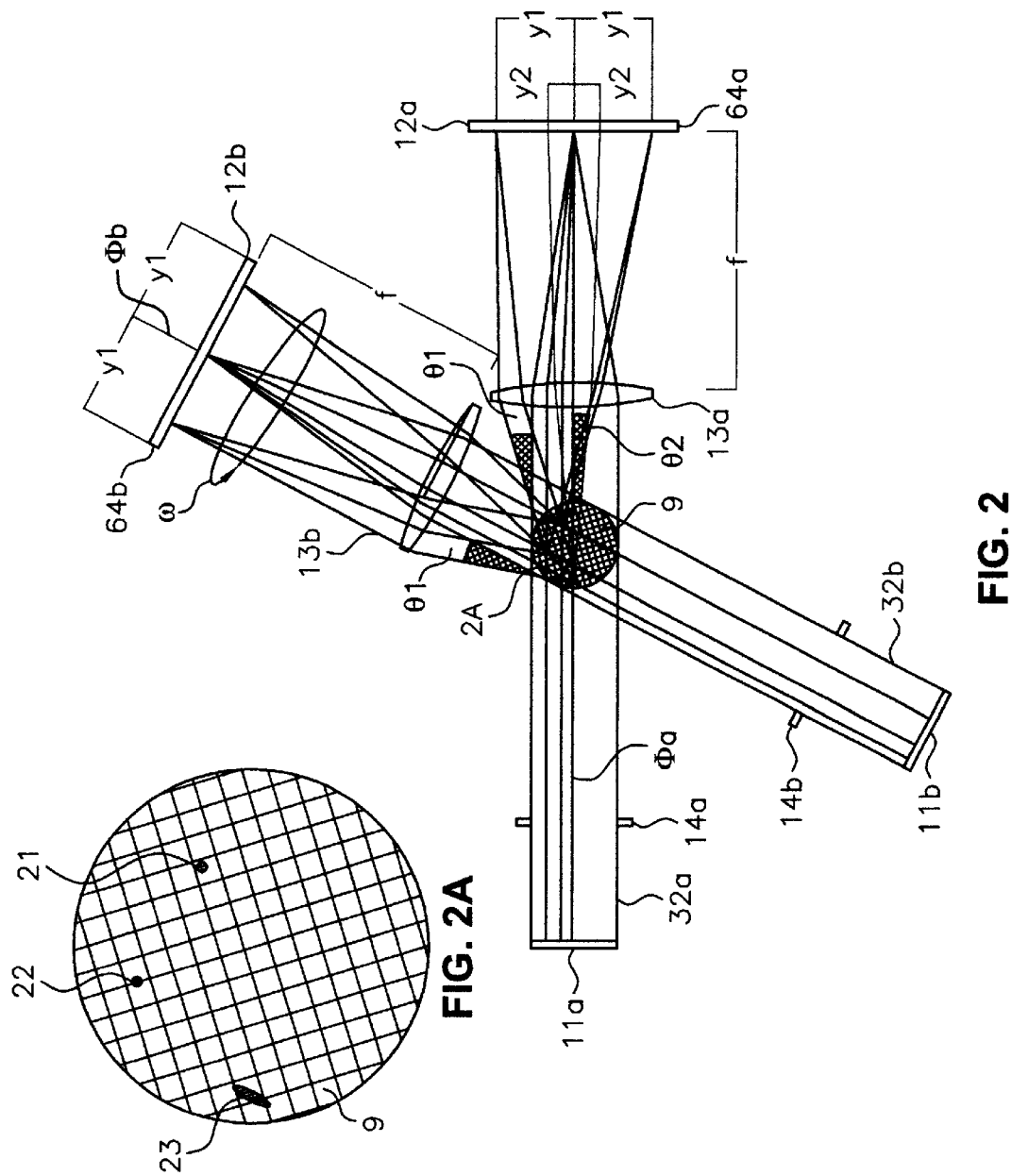
FIG. 2 schematically shows an example illustration of light rays as they pass through an object region in a three-dimensional imaging system, entering and exiting from two different viewing angles, as contemplated by an embodiment of the present invention.

Now referring to FIGS. 2 and 2A, one example embodiment of an optical tomography system for three-dimensional imaging in the Fourier Domain is illustrated. In FIG. 2, two viewpoints of a three-dimensional object region are shown, along with the distribution of the light in the Fourier planes. It will be understood that the illustrations herein are by way of example only and that the invention is not so limited. For example, while two viewpoints are shown schematically, the two viewpoints may be obtained by a plurality of optical imaging systems located at different viewpoints, by a single optical imaging system that is rotated into the varying views, or by rotating the object region before a single imaging optical system or multiple optical imaging systems, where the optical imaging systems are constructed in accordance with the teachings herein to use Fourier transforms for three-dimensional imaging.

The optical tomography system includes at least one collimated light source 11a, 11b, an object region 9 including at least one feature of interest 21, 22, 23, the object region being disposed in at least one optical path along optical axis $\Phi_a$ or $\Phi_b$ to be illuminated by the collimated light source 11a, 11b. At least one detector 12a, 12b is located in the at least one optical path along optical axis $\Phi_a$ or $\Phi_b$ to receive light passing through the object region 9. At least one lens 13a, 13b is located in the at least one optical path along optical axis $\Phi_a$ or $\Phi_b$ between the object region 9 and the at least one detector 12a, 12b such that a Fourier plane 64a, 64b is created in the back focal plane of each lens. The at least one detector 12a, 12b is located in the Fourier plane 64a, 64b for mapping a spatial frequency distribution of the at least one feature of interest.

In one example embodiment, the collimated light source 11a, 11b may comprise a monochromatic, collimated source 11 that emits a beam consisting of nearly parallel rays 32, such as may be produced by a high-quality gas laser. To reduce the signal due to unscattered light passing through the object region 9, an aperture 14a, 14b may advantageously be employed in each viewpoint.

FIG. 2 shows an example having a plurality of features 21, 22, and 23 within the object region 9, two being spheres and the third an ellipsoid. In a first viewpoint along the optical path along optical axis $\Phi_a$, each of the plurality of features 21, 22, and 23 appear identical, because the size and shape of their projections in the plane of the incident light are identical as registered by the detector 12a. Seen from a second viewpoint along the optical path along optical axis $\Phi_b$, however, the anisotropy of the third object 23 produces a diffraction pattern that differs from the diffraction pattern produced by the other two.

As shown in FIG. 2, placing an optical element, such as lens 13a or 13b or equivalent optical system, in an optical path along optical axis $\Phi_a$ or $\Phi_b$ between the object region 9 and the detector 12a or 12b creates a Fourier plane 64a, 64b as the case may be in the back focal plane of the lens, i.e., at a distance (f) from a lens of focal length f An image formed in the back focal plane thus comprises a Fourier transform of the light exiting the object region 9 in k-space, where k is a vector that signifies the direction of the light path. The image can be magnified, with the height above the optical axis, y, related to the scattering angle, θ, by:

$$y = f \sin \theta.$$

Note the rotational position, referenced as azimuth angle ω, of the ray about an optical axis, Φ, is the same in both the Fourier plane and the object region. Thus a point in the Fourier plane can be mapped to a specific direction of the rays in the object region, independent of the positions of those rays. Low spatial frequencies will pass through the Fourier plane close to the optical axis (i.e., near the point that maps into k=0), whereas high spatial frequencies will pass through further from the optical axis. By placing an array of detector elements in this plane, the power distribution of the two-dimensional Fourier transform can be acquired. If the object region or the source-detector pair is then rotated about a central axis, additional two-dimensional Fourier transforms can then be acquired for each new viewpoint.

Having described the apparatus of the invention, further understanding will be promoted by describing its operation. In operation, each of the at least one collimated light source 11a, 11b emits a beam consisting of nearly parallel rays 32a, 32b. The nearly parallel rays 32a, 32b may be subjected to spatial filtering prior to reaching an object region 9, so as to remove any divergent light. To reduce the signal due to unscattered light passing through the object region 9, an aperture 14 may advantageously be employed. A lens 13a is located in the optical path between the object region 9 and the detector 12a, such that a Fourier plane will be created in the back focal plane of the lens. By placing an array of detector elements 12a in the Fourier plane, the spatial frequency distribution due to the features 21, 22, and 23 can be mapped.

From a second viewpoint, all three features 21, 22, and 23 scatter the incoming light from 11b into an angle $\theta_1$, such that the detector 12b registers the same intensity distribution for all three features, having (for this schematic representation) a central peak and a second peak at a radius $y_1$ from the center. From viewpoint a, however, the anisotropy of feature 23 is apparent; it scatters into angle $\Phi_2$, producing side peaks at a radius $y_2$ from the center, while features 21 and 22 continue to produce side peaks at a radius $y_1$ due to light scattered into angle $\Phi_1$.

Figure 3:
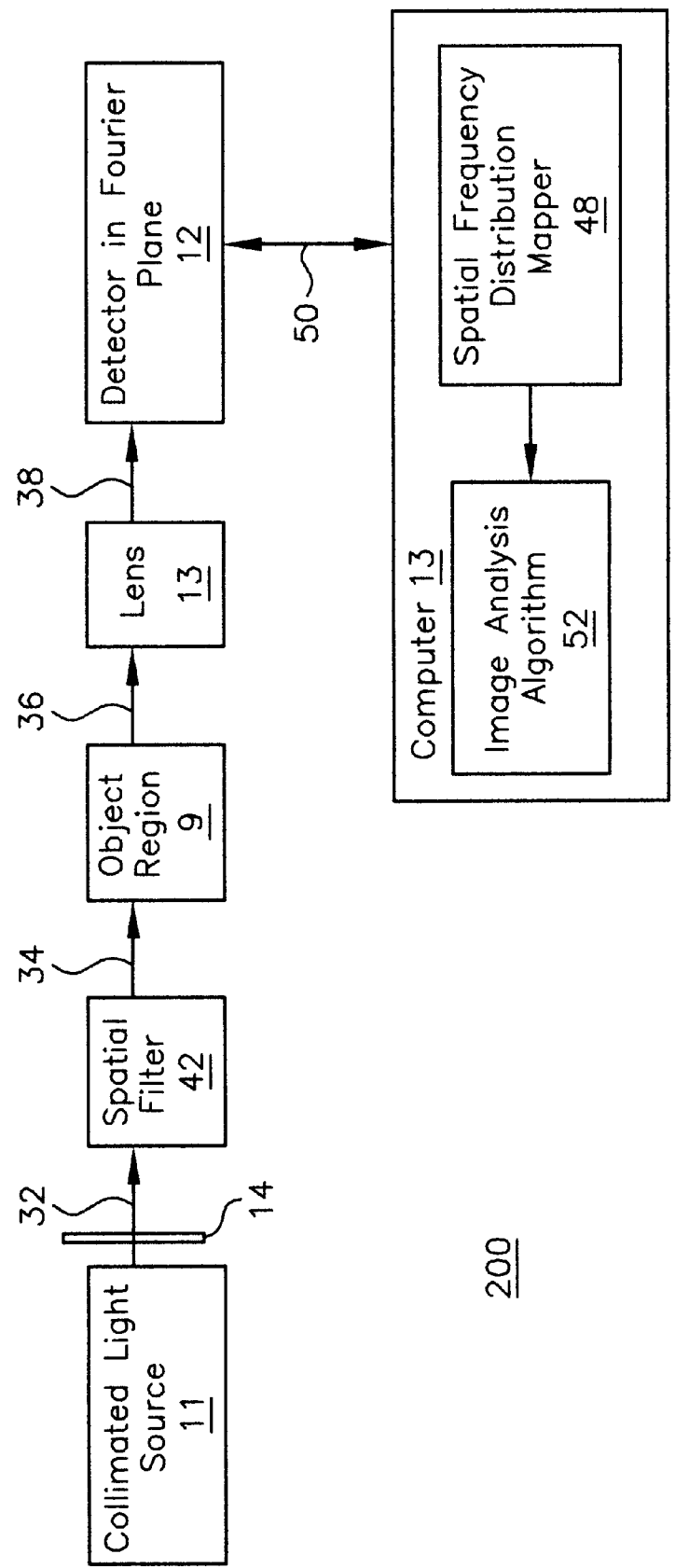
FIG. 3 schematically shows an example illustration of a high level block diagram of a method and apparatus for three-dimensional imaging in the Fourier Domain as contemplated by the present invention.

Referring to FIG. 3, there schematically shown is an example illustration of a high level block diagram of a multi-dimensional imaging system 200 using the method and apparatus for three-dimensional imaging in the Fourier Domain as contemplated by the present invention. The multi-dimensional imaging system 200 includes a collimated light source 11, an optional aperture 14, an optional spatial filter 42, an object region 9, at least one lens or equivalent optics 9, at least one detector 12, and a computer 13. In one example embodiment, the computer 13 may comprise a personal computer or workstation including a conventionally designed computer program serving as a spatial frequency distribution mapper 48 and an image analysis algorithm for producing three-dimensional images or correlation functions from two-dimensional Fourier transforms. The collimated light source 11 generates nearly parallel light rays 32 that are filtered by optional spatial filter 42. Filtered light 34 illuminates the object region 9. Transmitted light rays 36 are transmitted through the object region and pass through lens 13. Lens 13 transmits back plane light rays 38 onto a back focal plane so as to impinge on detector 12 located in the Fourier plane. Information 50 is transmitted between the computer 13 and the detector 12. The detector 12 may advantageously comprise, for example, image sensors, such as, for example, CCD or CMOS solid state image sensors, detector arrays and the like.

Figure 4:
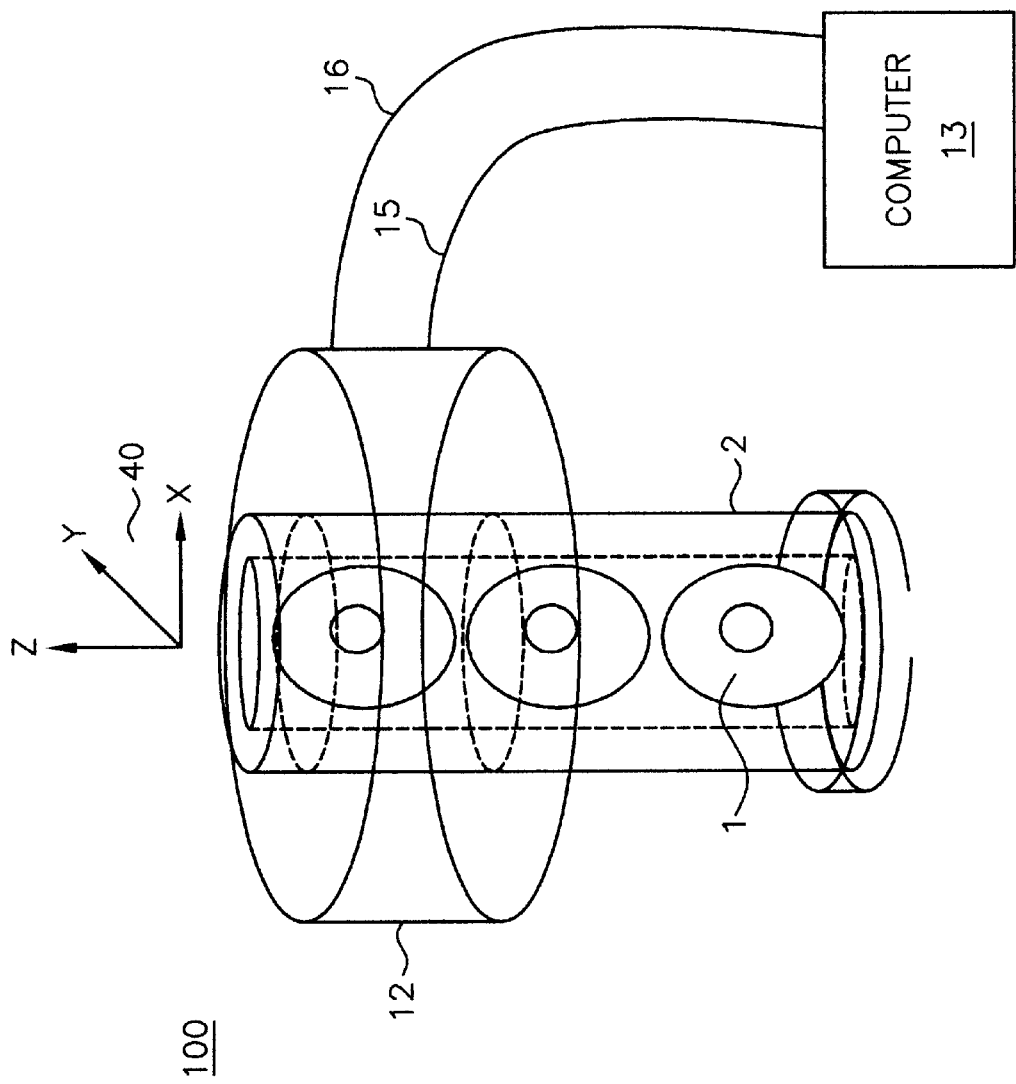
FIG. 4 schematically shows an example illustration of an optical tomography system employing a system for three-dimensional imaging in the Fourier Domain as contemplated by the present invention.

Referring to FIG. 4, there schematically shown is an example illustration of an optical tomography system employing a system for three-dimensional imaging in the Fourier Domain as contemplated by the present invention. The optical tomography (OT) system 100 includes in one example embodiment a reconstruction cylinder 12, positioned around object containing tube 2. The object containing tube 2 may, for example, comprise a cell entrainment tube wherein the cell is held in a gel, or a capillary tube for cell flow, depending on the type of optical tomography system.

The OT system 100 is oriented with reference to a coordinate system 40 having coordinates in the X, Y and Z-directions. In operation, an object of interest 1, such as, for example a cell, including a human cell, is held, or flows through, an object containing tube 2. It will be understood that lines 15 and 16 are representative of communication and control lines between the OT system 100 and a computer 13 that communicate data, image information, control signals and other signals between the computer and the OT system 100. The reconstruction cylinder 12 may advantageously comprise a system for multi-dimensional imaging using Fourier transforms as described hereinabove with reference to FIG. 2. Signals from the reconstruction cylinder 12 may be analyzed directly or processed using known image processing, image analysis and/or computerized tomographic image reconstruction techniques to provide two-dimensional or three-dimensional information about cells and other objects of interest.

In a further embodiment, the object region can be located between the at least one lens or equivalent optics and its back focal plane, such that an approximation of the Fourier transform of the light exiting the object region is formed in the back focal plane. This approximate Fourier transform can be considered as equivalent to an exact Fourier transform provided that the maximum angle of the convergent light (i.e., the numerical aperture of the optical system), the maximum scattering angle of interest (as measured relative to the incident light ray that is scattered), and the thickness of the object region are small enough to allow all the light scattered at an individual angle (relative to the light ray causing the scattering) to reach a single detector element.

In further embodiments, Parseval's Theorem can be applied to generate auto-correlation and cross-correlation functions of the object region. To generate the autocorrelation function, it is sufficient to measure the intensity, $|F(g)|^2$, of the light in the back focal plane of the at least one optical element. To generate the cross-correlation function, a mask, formed from the diffraction pattern obtained from a different object, can be placed in the back focal plane of the at least one optical element.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

What is claimed is:

1. A method for multi-dimensional imaging of an object region, the method comprising the steps of:
   a) passing light through an object region to produce transmitted light rays;
   b) capturing the light rays by at least one optical element, the at least one optical element having a back focal plane;
   c) using at least one detector to capture a power spectrum of a two-dimensional Fourier transform, where the at least one detector is located in a back focal plane of the at least one optical element; and d) repeating steps a)–c) for two or more viewpoints about an arc at least partially encircling the object region to obtain multiple two-dimensional Fourier transforms.

2. The method of claim 1, further comprising the step of using an image analysis computer algorithm to extract features of interest from one or more of the multiple two-dimensional Fourier transforms.

3. The method of claim 1 wherein the optical element is selected from the group consisting of a lens and reflective surface.

4. The method of claim 1 further comprising the step of passing the light through a spatial filter placed in an optical path between the light source and the object region.

5. The method of claim 1, in which the light rays captured by the at least one optical element are transmitted through the object region prior to passing through the at least one optical element.

6. The method of claim 1, in which the light rays pass through the object region after passing through the at least one optical element.

7. The method of claim 1, further comprising the step of reconstructing the multiple two-dimensional Fourier transforms to create a three-dimensional Fourier transform.

8. The method of claim 7, further comprising the step of using an image analysis computer algorithm to extract features of interest from the three-dimensional Fourier transforms.

9. The method of claim 7, further comprising the step of employing a mask and an image analysis algorithm to construct of a cross-correlation function of the object region with a previously examined object region.

10. The method of claim 9, in which the previously examined object region is a cell.

11. The method of claim 9, in which the previously examined object region is an artificially generated phantom.

12. The method of claim 7, further comprising the step of employing an image analysis algorithm to construct of an autocorrelation function of the object region.

13. A system for multi-dimensional imaging of an object region, the system comprising:

a light source;

an object region including at least one feature of interest the object region being disposed in an optical path to be illuminated by the light source;

at least one detector located in the optical path to receive light passing through the object region;

at least one lens located in the optical path between the object region and the at least one detector such that a Fourier plane is created in the back focal plane of the lens, where the at least one detector is located in the Fourier plane; and wherein the light source, the at least one detector and the at least one lens are arranged to provide multiple views of the object region for mapping at least one n-dimensional spatial frequency distribution of the at least one feature of interest at each view so as to provide a plurality of spatial frequency distributions used for constructing an (n+1)-dimensional data set, where n is greater than or equal to 1, whereby an n-dimensional Fourier transform may be reconstructed as an (n+1)-dimensional Fourier transform.

14. The system of claim 13 wherein the light source comprises a laser.

15. The system of claim 13 further comprising a spatial filter placed in an optical path between the light source and the object region.

16. The system of claim 13 further comprising an aperture placed in an optical path between the light source and the object region.

17. The system of claim 13 wherein the at least one detector comprises a detector selected from the group consisting of CCD, CMOS, solid state image sensors, and solid state image sensor detector arrays.

18. A parallel-beam optical tomography system for imaging an object of interest having at least one feature of interest, the parallel-beam optical tomography system comprising:

a light source projecting a column of light along an optical path;

an object containing tube located along the optical path, wherein the object of interest is held within the object containing tube;

at least one detector array, where the at least one detector array is located to receive emerging radiation from the object of interest;

at least one lens located in the optical path between the object of interest and the at least one detector array such that a Fourier plane is created in a back focal plane of the lens, where the at least one detector is located in the Fourier plane; and wherein the light source, the at least one detector and the at least one lens are arranged to provide multiple views of the object region for mapping at least one n-dimensional (n>1) spatial frequency distribution of the at least one feature of interest at each view so as to provide a plurality of spatial frequency distributions used for constructing an (n+1)-dimensional data set, where n is greater than or equal to 1, whereby an n-dimensional Fourier transform maybe reconstructed as an (n+1)-dimensional Fourier transform.

19. The system of claim 18 wherein the at least one detector comprises a detector selected from the group consisting of CCD, CMOS, solid state image sensors, and solid state image sensor detector arrays.

20. The parallel-beam optical tomography system of claim 18 wherein the object of interest comprises a cell.

21. The system of claim 18 wherein the light source comprises a laser.

22. The system of claim 18 further comprising a spatial filter placed in the optical path between the light source and the object region.

23. The system of claim 18 further comprising an aperture placed in the optical path between the collimated light source and the object region.

* * * * *